(12) United States Patent
Trieu (10) Patent No.: US 8,945,223 B2
(45) Date of Patent: Feb. 3, 2015

(54) IN-SITU FORMABLE NUCLEUS PULPOSUS IMPLANT WITH WATER ABSORPTION AND SWELLING CAPABILITY

(75) Inventor: Hai H. Trieu, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1696 days.

(21) Appl. No.: 11/072,971

(22) Filed: Mar. 7, 2005

(65) Prior Publication Data
US 2005/0203206 A1 Sep. 15, 2005

(51) Int. Cl.
*A61F 2/44* (2006.01)
*A61B 17/16* (2006.01)
*A61L 27/26* (2006.01)
*A61L 27/50* (2006.01)
(Continued)

(52) U.S. Cl.
CPC ............... *A61F 2/442* (2013.01); *A61L 27/26* (2013.01); *A61L 27/50* (2013.01); *A61L 27/52* (2013.01); *A61F 2002/30075* (2013.01); *A61F 2002/30131* (2013.01); *A61F 2002/30594* (2013.01); *A61F 2002/30596* (2013.01); *A61F 2002/30677* (2013.01); *A61F 2002/3082* (2013.01); *A61F 2002/444* (2013.01); *A61F 2210/0061* (2013.01); *A61F 2230/0013* (2013.01); *A61L 2400/06* (2013.01); *A61L 2430/38* (2013.01)
USPC .................. 623/17.12; 128/898; 606/151

(58) Field of Classification Search
CPC ............... A61F 2/00; A61F 5/00; A61F 9/00; A61F 13/00; A61F 2002/00; A61F 2210/00; A61F 2220/00; A61B 1/00; A61B 7/00; A61B 2010/00; A61B 2217/00; A61B 2218/00; A61L 2/00; A61L 15/00; A61L 2202/00; A61L 2209/00
USPC .............................. 623/17.11–17.17
See application file for complete search history.

(56) References Cited

U.S. PATENT DOCUMENTS 3,730,947 A 5/1973 Stoffey et al.
4,102,856 A 7/1978 Lee, Jr.
(Continued)

FOREIGN PATENT DOCUMENTS

EP 0 662 309 A1 7/1995
WO WO 98/20939 A 5/1998
WO WO 2006/004940 A2 1/2006

OTHER PUBLICATIONS

Alberto Di Martino, et al. *Nucleus Pulposus Replacement, Basic Science and Indications for Clinical Use*; SPINE, vol. 30, No. 16; Aug. 15, 2005 (pp. S16-S22).

*Primary Examiner* — David Isabella
*Assistant Examiner* — Ann Schillinger
(74) *Attorney, Agent, or Firm* — Sorell Lenna & Schmidt LLP (57) ABSTRACT

Embodiments of the invention relate to a curable nucleus pulposus implant having water absorption and swelling capabilities, compositions for producing the curable nucleus pulposus implants, and methods of using the curable nucleus pulposus implants. The curable nucleus pulposus implant can be created from a polymer blend composition comprising a ratio of a curable material and at least one hydrophilic polymer. The resulting polymer blend composition may be used to generate curable nucleus pulposus implants to treat a number of disease and/or disorders, such as herniated discs. The curable nucleus pulposus implants may further contain polyelectrolytes and elastomer compounds, as well as pharmacological and biological agents.

34 Claims, 3 Drawing Sheets

(51) Int. Cl.
*A61L 27/52* (2006.01)
*A61F 2/30* (2006.01)

(56) References Cited

U.S. PATENT DOCUMENTS

| | | | |
|---|---|---|---|
| 4,131,729 A | 12/1978 | Schmitt et al. | |
| 4,273,873 A * | 6/1981 | Sugitachi et al. | 435/180 |
| 5,462,797 A * | 10/1995 | Williams et al. | 428/345 |
| 5,556,429 A | 9/1996 | Felt | |
| 5,888,220 A | 3/1999 | Felt et al. | |
| 5,899,939 A * | 5/1999 | Boyce et al. | 623/16.11 |
| 6,187,048 B1 * | 2/2001 | Milner et al. | 623/17.12 |
| 6,255,362 B1 * | 7/2001 | Ito | 523/107 |
| 6,264,695 B1 * | 7/2001 | Stoy | 623/17.16 |
| 6,296,607 B1 | 10/2001 | Milbocker | |
| 6,306,177 B1 * | 10/2001 | Felt et al. | 623/23.6 |
| 6,332,894 B1 | 12/2001 | Stalcup et al. | |
| 6,339,113 B1 | 1/2002 | Han et al. | |
| 6,416,776 B1 | 7/2002 | Shamie | |
| 6,419,704 B1 * | 7/2002 | Ferree | 623/17.12 |
| 6,428,576 B1 * | 8/2002 | Haldimann | 623/17.16 |
| 6,458,889 B1 * | 10/2002 | Trollsas et al. | 525/54.1 |
| 6,533,799 B1 * | 3/2003 | Bouchier | 606/192 |
| 6,533,819 B1 | 3/2003 | Urry et al. | |
| 6,624,245 B2 * | 9/2003 | Wallace et al. | 525/54.1 |
| 6,632,235 B2 * | 10/2003 | Weikel et al. | 606/192 |
| 6,660,827 B2 | 12/2003 | Loomis et al. | |
| 6,746,485 B1 * | 6/2004 | Zucherman et al. | 623/17.16 |
| 7,004,970 B2 * | 2/2006 | Cauthen, III et al. | 623/17.16 |
| 7,077,865 B2 * | 7/2006 | Bao et al. | 623/17.12 |
| 2002/0049363 A1 | 4/2002 | Milbocker | |
| 2002/0082699 A1 * | 6/2002 | Ward et al. | 623/17.16 |
| 2002/0120033 A1 * | 8/2002 | Jia et al. | 523/115 |
| 2003/0009235 A1 * | 1/2003 | Manrique et al. | 623/23.63 |
| 2003/0125499 A1 * | 7/2003 | Benz et al. | 528/44 |
| 2003/0220649 A1 | 11/2003 | Bao et al. | |
| 2003/0220695 A1 * | 11/2003 | Sevrain | 623/17.16 |
| 2004/0033251 A1 * | 2/2004 | Sparer et al. | 424/425 |
| 2004/0068078 A1 | 4/2004 | Milbocker | |
| 2004/0117019 A1 | 6/2004 | Trieu et al. | |
| 2004/0166088 A1 * | 8/2004 | Shalaby | 424/78.29 |
| 2004/0220296 A1 * | 11/2004 | Lowman et al. | 523/113 |
| 2005/0113919 A1 * | 5/2005 | Cragg et al. | 623/17.11 |
| 2005/0234425 A1 * | 10/2005 | Miller et al. | 604/508 |
| 2005/0283220 A1 * | 12/2005 | Gobran et al. | 623/1.4 |
| 2006/0173464 A1 * | 8/2006 | Ellman et al. | 606/93 |

* cited by examiner

IN-SITU FORMABLE NUCLEUS PULPOSUS IMPLANT WITH WATER ABSORPTION AND SWELLING CAPABILITY

FIELD OF THE INVENTION

Embodiments of the invention relate to a curable nucleus pulposus implant with water absorption and swelling capabilities. The nucleus pulposus implant can be created from a polymer blend composition comprising a ratio of an injectable/in-situ curable polymer (hereinafter the "curable material") and at least one hydrophilic polymer. The resulting polymer blend composition can be used to generate nucleus pulposus implants for the treatment of diseases and/or disorders, such as herniated discs. The nucleus pulposus implants may further contain polyelectrolytes and elastomer compounds, as well as pharmacological and biological agents.

BACKGROUND OF THE INVENTION

The human spine includes intervertebral discs that are located between adjacent vertebrae of the spine. The intervertebral discs function to stabilize the spine and distribute forces between vertebrae. Intervertebral discs comprise three regions, known as the annulus fibrosus, the nucleus pulposus, and the cartilagenous end plates.

The nucleus pulposus retains a gelatinous consistency, and includes a high proteoglycan content. The nucleus pulposus further retains approximately 70 to 90% water, aiding in its fluid nature. The nucleus pulposus is contained within the annulus fibrosus. The annulus fibrosus retains a more rigid consistency, and is composed primarily of type I and type II collagen. The annulus fibrosus functions to provide peripheral mechanical support to the intervertebral discs, torsional resistance, and resistance to the hydrostatic pressures of the nucleus pulposus.

Intervertebral discs may be displaced or damaged due to trauma or disease. Disruption of the annulus fibrosus may allow the nucleus pulposus to protrude into the vertebral canal, a condition commonly referred to as a herniated or ruptured disc. The extruded nucleus pulposus may press on a spinal nerve, resulting in nerve damage, pain, numbness, muscle weakness and paralysis. Intervertebral discs also may deteriorate due to the normal aging process. As a disc dehydrates and hardens, the disc space height will be reduced, leading to instability of the spine, decreased mobility, and pain.

One way to relieve the symptoms of these conditions is by surgical removal of a portion or all of the intervertebral disc. The removal of the damaged or unhealthy disc may allow the disc space to collapse, which would lead to instability of the spine, abnormal joint mechanics, nerve damage, as well as severe pain. Therefore, after removal of the disc, adjacent vertebrae are sometimes fused to preserve the disc space. Spinal fusion involves inflexibly connecting adjacent vertebrae through the use of bone grafts or metals rods. Because the fused adjacent vertebrae are prevented from moving relative to one another, the vertebrae no longer contact each other in the area of the damaged intervertebral disc and the likelihood of continued irritation is reduced. Spinal fusion, however, is disadvantageous because it restricts the patient's mobility by reducing the spine's flexibility.

Attempts to overcome these problems have led researchers to investigate the efficacy of implanting an artificial device to replace the damaged portion of the patient's intervertebral disc. One such prosthesis is an artificial implantable nucleus replacement device. Nucleus implants are used when the nucleus pulposus of the intervertebral disc is damaged but the annulus fibrosis and vertebral end-plates are still sufficiently healthy to retain. Nucleus replacement surgery involves removing the damaged nucleus pulposus of the intervertebral disc and insertion of the nucleus implant inside of the retained annulus fibrosis. The nucleus implant is often a molded polymer device designed to absorb the compressive forces placed on the spine. For increased strength, the nucleus implant may be combined with an internal matrix of, for example, biocompatible fibers. The retained annulus fibrosis provides tensile strength. Some desirable attributes of a hypothetical implantable nucleus replacement device include axially compressibility for shock absorbance, excellent durability to avoid future replacement, and bio-compatibility.

The description herein of problems and disadvantages of known apparatus, methods, and devices is not intended to limit the invention to the exclusion of these known entities. Indeed, embodiments of the invention may include one or more of the known apparatus, methods, and devices without suffering from the disadvantages and problems noted herein.

SUMMARY OF THE INVENTION

There remains a need for synthetic compositions useful for nucleus pulposus replacement to alleviate injury due to failure of an intervertebral disc. It therefore is a feature of an embodiment of the invention to provide a nucleus implant that has improved water absorption and swelling capabilities upon insertion into a disc space.

In accordance with these and other features of embodiments of the invention, there is provided a nucleus pulposus implant composition comprising a mixture of a polymerizable polymer material and at least one hydrophilic polymer, wherein the polymerizable polymer material and the at least one hydrophilic polymer are present in a weight ratio of about 1:1 to about 19:1, respectively.

In accordance with another feature of an embodiment of the invention, there is provided a method of making a nucleus pulposus implant in-situ in a patient in need thereof, comprising mixing a polymerizable polymer material and at least one hydrophilic polymer in a weight ratio of from about 1:1 to about 19:1, and polymerizing the polymerizable polymer inside the patient to form the nucleus pulposus implant.

In accordance with yet another feature of an embodiment of the invention, there is provided a method of treating or preventing a disease or disorder comprising surgically evacuating at least a portion of endogenous nucleus pulposus material and any free disc fragments from a disc space. The method also includes producing a nucleus pulposus implant as described above.

These and other features of the embodiments will be readily apparent from the detailed description that follows.

DETAILED DESCRIPTION OF PREFERRED EMBODIMENTS

For the purposes of promoting an understanding of the present invention, reference will now be made to preferred embodiments and specific language will be used to describe the same. The terminology used herein is for the purpose of describing particular embodiments only, and is not intended to limit the scope of the present invention. As used throughout this disclosure, the singular forms "a," "an," and "the" include plural reference unless the context clearly dictates otherwise. Thus, for example, a reference to "a spinal implant" includes a plurality of such implants, as well as a single implant, and a reference to "a therapeutic agent" is a reference to one or more therapeutic and/or pharmaceutical agents and equivalents thereof known to those skilled in the art, and so forth.

As used herein, "hydrophilic" shall mean a material or substance having an affinity for water.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the various spinal implants, therapeutic and/or pharmaceutical agents, and other components that are reported in the publications and that might be used in connection with the invention. Nothing herein is to be construed as an admission that the invention is not entitled to antedate such disclosures by virtue of prior invention.

Spinal nucleus implants of the embodiments preferably are produced from polymer compositions comprising a mixture or blend of polymers. Throughout this description, the terms "mixture" and "blend" will be used interchangeably. Nucleus pulposus implants of the invention preferably are produced from polymer blend compositions. The polymer blend composition comprises, or alternatively consists of, a ratio of a polymerizable or curable material and at least one hydrophilic polymer.

In one embodiment of the invention, the polymer composition comprises, or alternatively consists of, a mixture of polymerizable material and a hydrophilic polymer, wherein the ratio of the polymerizable material to the at least one hydrophilic polymer is within the range of from 1:1 to about 19:1, respectively. In a preferred embodiment, the polymerizable material and the at least one hydrophilic polymer exist as a mixtuer in a weight ratio from about 3:1 to about 9:1, and even more preferably in a weight ratio from about 4.5:1 to about 7:1.

In another embodiment, the mixture of polymerizable material and the at least one hydrophilic polymer is, preferably, a confluent blend where the at least one hydrophilic polymer is consistently dispersed throughout the polymerizable material. Skilled artisans will appreciate various mechanisms by which the respective components of the polymer mixture may be mixed prior to insertion into a patient for curing so as to produce an implant having desirable properties. For example, the ratio of respective components can be varied by adjusting the amounts of each component added so that one portion, (e.g., the posterior side of the implant) may have a greater weight ratio of polymerizable material than another portion (e.g., the anterior side of the implant).

While not intending on being bound by any theory of operation, it is believed that the ratio of the hydrophilic polymer(s) described herein to the polymerizable material enables the resulting blend to absorb significant amounts of water, once the polymer composition cures in a hydrated environment such as the human body. The absorption of water results in swelling of the composition material, and an increase in the mechanical properties of the composition, an increase in the durability and an increase in the biostability of the composition. The polymerizable material provides structural support for the nucleus pulposus implant. The polymerizable material component of the nucleus pulposus implant is believed to prevent deformation, cracks, tears, breakage or other damage.

Any polymerizable material may be used in the invention so long as it is capable of polymerizing to form a solid or semi-solid (e.g., gel) like mass, and preferably is capable of being administered to a patient as a liquid, or gel-like material, and then capable of curing inside the patient's body to form the nucleus pulposus implant. Throughout this description, the terms "curable" and "polymerizable" will be used interchangeably, unless otherwise indicated. The polymerizable material may be a monomer, oligomer, or material capable of undergoing cross-linking either by itself, or with the aid of cross-linking agents or external force (e.g., heat, light, water, etc.). Self-curing polymerizable materials include epoxy materials, polyisobutylene rubbers, and other self-cross linking polymers known to those skilled in the art. Moreover, one who is skilled in the art will recognize that the state in which the polymerizable material is used for purposes of this invention may be chosen to correspond with the particular conditions expected during disc reconstruction or repair.

Preferably, the curable material is a liquid that can be readily injected into the patient, and then cures in a relatively short period of time inside the patient. A preferred polymerizable material used with the invention comprises, or alternatively consists of, a prepolymer component that is admixed with a curative agent prior to administration to the patient, and the admixture of prepolymer and curative agent cures in situ to produce the nucleus pulposus implant. The hydrophilic polymer component of the polymer blend composition preferably is mixed with either the prepolymer component or the curative component of the curable material prior to admixture of the prepolymer component and curative component. Alternatively, the hydrophilic polymer component may be added separately to the patient and mixed in-situ to form the swellable nucleus pulposus implant of the invention.

Any polymerizable material may be used as the curable material in the invention so long as it is capable of forming a suitable intervertebral disc repair device upon polymerization. In accordance with one embodiment of the present invention, the polymerizable material is a water-activated polymer. In one preferred embodiment, contact with body fluids after implantation initiates the polymerization reaction. In another preferred embodiment, water or saline solution may be injected into the polymer blend after implantation.

In one preferred embodiment, the polymerizable material may be a polyfunctional isocyanate based prepolymer wherein water can be used to effect polymerization by causing the formation of urea linkages. Blocked isocyanate prepolymers which, on crosslinking with an active prepolymer, can polymerize about or below body temperature also may be used. An example of this type of system is a polyurethane resin containing blocked isocyanate groups based on toluene diisocyanate and p-isononyl phenol reacted with a polyfunctional amine terminated polymer such as polyalkylene oxide amine terminated polymer (e.g. JEFFAMINE D2000®, commercially available from Texaco Chemicals, San Francisco, Calif.). The hydrophilicity of these systems may be varied by reaction of the blocked isocyanate resin with polyfunctional amine terminated polymers which contain a high proportion of ethylene oxide (e.g. JEFFAMINE ED-600®, commercially available from Texaco Chemicals, San Francisco, Calif.). Alternatively the blocked isocyanate polyurethane prepolymers may be prepared using polyols with high ethylene oxide content.

Another alternative is to use siloxanes comprising functional groups which allow polymerization of the siloxanes with water to occur (e.g. alkoxy, acyloxy, amido, oximo or amino groups). Acyloxy, acetoxy and alkoxy functionalities are most frequently employed. The number of siloxane groups may be determined such that the cured polymer is a resiliently deformable material.

In another embodiment of the present invention, the polymerizable material may be a two-part polymerizable material. In a preferred embodiment, the two-part polymerizable material forms a polyurethane and has as Part I an isocyanate-functional polyurethane pre-polymer (optionally referred to as an "quasi-polymer"). The quasi-polymer of Part I typically includes a polyol component in combination with a hydrophobic additive component and an excess of an isocyanate component. Part II of the two-part polymerizable material may include long-chain polyols, chain extenders, or cross-linkers, together with other ingredients (e.g., catalysts, stabilizers, plasticizers, antioxidants, dyes and the like). Such adjuvants or ingredients may be added to or combined with any other component thereof either prior to or at the time of mixing, delivery, and/or curing.

The isocyanate component may be provided in any suitable form, examples of which include 2,4'-diphenylmethane diisocyanate, 4,4'-diphenylmethane diisocyanate, toluene diisocyanates, and mixtures or combinations of these isomers, optionally together with small quantities of 2,2'-diphenylmethane diisocyanate. Other examples include aromatic polyisocyanates and their mixtures or combinations, such as are derived from phosgenation of the condensation product of aniline and formaldehyde. An isocyanate that has low volatility, such as diphenylmethane diisocyanate, rather than more volatile materials such as toluene diisocyanate, may be used. An example of a particularly suitable isocyanate component is the 4,4'-diphenylmethane diisocyanate ("MDI"), preferably provided in liquid form as a combination of 2,2'-, 2,4'- and 4,4'-isomers of MDI.

The polyol component may be provided in any suitable form as well. As used herein, the term "polyol" includes virtually any functional compound having active hydrogens in accordance with the well-known Zerevitinov test, as described for instance in Chemistry of Organic Compounds by Carl R. Noller, Chapter 6, pp. 121-122 (157). Thus, for example, amine terminated polyethers and polyolefins, thiols, polyimines, and polyamines also can be used as polyols in the present invention. Suitable polyols for use in preparing a composition of this invention also include polyalkylene ethers derived from the condensation of alkylene oxides (e.g., ethylene oxide, propylene oxide, and blends thereof), as well as tetrahydrofuran based polytetramethylene ether glycols, polycaprolactone polyols, polycarbonate polyols and polyester polyols. Examples of suitable polyols include polytetrahydrofuran polyol ("PTHF", also known as polytetramethylene oxide ("PTMO") or polytetramethylene ether glycol ("PT-MEG")).

In a further preferred embodiment of the present invention, the two-part polymerizable material forming a polyurethane contains one or more, and more preferably two or more, biocompatible catalysts that can assist in controlling the curing process during one or more of the following periods: (1) the induction period, (2) the setting period, and finally, (3) the final cure of the biomaterial. Together these three periods, including their absolute and relative lengths, and the rate of acceleration or cure within each period, determine the cure kinetics or profile. Examples of suitable catalysts include tin compounds (such as tin esters, tin alkylesters, and tin mercaptides), amines, such as tertiary amines and the like. An example of a suitable catalyst system is a combination of a tin catalyst (e.g., COTIN 222®, available commercially from Cascam Company, Bayonne, N.J.) and a tertiary amine (e.g., DABCO(TEDA)®, a triethylene diamine catalyst available commercially from Air Products, Allentown, Pa.). These components can be used in any suitable ratio, e.g., between about 1:1 parts and about 1:5 parts of the tin catalyst and the diamine, respectively.

In yet another further preferred embodiment of the present invention, the two-part polymerizable material forming a polyurethane comprises a diisocyanate, a polyalkylene oxide, and low molecular diols as chain extenders. The final polymer having a hard segment content of about 25 to about 50% by weight, and preferably of about 30 to about 40% by weight, based on the weight of the diisocyanate and chain extender. Optionally, one or more catalysts may be incorporated into one or more components of the biomaterial in order to polymerize the biomaterial in the physiological environment within a desired length of time. Preferably, biomaterials of the present invention are able to polymerize (i.e., to the point where distraction means can be removed and/or other biomaterial added), within 5 minutes or less, and more preferably within on the order of 3 minutes or less.

In another preferred embodiment of the present invention, the two-part polymerizable material may comprise mixtures of poly(hydroxyalkyl(meth)acrylates) and poly(alkyl(meth)acrylates) crosslinked using polyfunctional (meth)acrylate monomers or oligomers, (e.g. triethyleneglycol dimethacrylate). The reagent may be cured at low temperature by using a free radical initiator and an amine activator (e.g. benzoyl peroxide and dimethyl p-toluidene). Preferably the alkyl groups contain from 1 to 4 carbon atoms.

In another preferred embodiment of the present invention, the two-part polymerizable material may comprise a mixture of tetra and trifunctional epoxy resin blend reacted with multifunctional amines and amino terminated elastomers such as an epoxy terminated silane and an amino terminated nitrile rubber. The two-part polymerizable material may comprise a monomer oligomer or polymer which contains ethylenic unsaturation. The ethylenic unsaturation may be acrylic or methacrylic unsaturation.

In another embodiment of the present invention, polymer complexes may be used, e.g., complexes formed between the following polyanions, poly (sodium acrylate), poly(sodium vinyl sulphate) sodium poly phosphates, sodium polystyrene sulphonate and the following polycations: poly(N,N,N-trialkylammonioalkylacrylate), poly(N-alkylpyridinium) cation. There are several natural polymers that are capable of forming complexes. Anionic polymers include: sodium carboxymethyl cellulose, sodium cellulose sulphate, sodium alginate, sodium hyaluronate. Cationic polymers include chitosan, quaternised chitosan, amino alkylated and subsequently quarternised cellulose, poly-L-lysine, and mixtures thereof.

In another embodiment of the present invention, the polymerizable materials are heat-activated to initiate polymerization. The temperature at which the polymerizable material is activated should be lower than or equal to body temperature so that the internal heat of the body will cause the polymerization reaction to initiate. The heat-activated polymerizable material may either soak the porous matrix before insertion into the evacuated disc space or be injected into the porous matrix after the matrix has been inserted into the evacuated disc space.

In another embodiment of the present invention, the polymerizable materials are light-activated to initiate polymerization. The light-activated polymerizable materials may be chosen such that the wavelengths of light used to initiate the polymerization reaction do not interact with or damage surrounding body tissues. For example, the polymerizable material may include any of the known photopolymerizable systems employed in photography (e.g., including ethylenically unsaturated compounds and photo-initiators), or those used in forming dental materials. A suitable material includes a one-part composition comprised of a polyfunctional urethane methacrylate and/or polyfunctional urethane acrylate and a polyfunctional acrylate resin. Urethane methacrylate is the product of the reaction of a diisocyanate with an OH-functional methacrylate, such as hydroxyethyl methacrylate for example. When a diisocyanate is used, the product is a urethane dimethacrylate; if an OH-functional acrylate is used, such as a hydroxyethyl acrylate, a difunctional acrylate is the result, similarly to the methacrylate. Such a urethane methacrylate or urethane acrylate, especially a urethane dimethacrylate is advantageous, because among other things it offers superior material properties such as great stiffness or low moisture absorption. Also possible is the use of a monomer prepared from the combination of triisocyanates or higher isocyanates with OH-functional acrylates or methacrylates, in which case these urethane methacrylates or urethane acrylates will have a functionality of 3 or more. Advantageously, the urethane methacrylate is a urethane dimethacrylate or urethane trimethacrylate and the urethane acrylate is a urethane diacrylate or a urethane triacrylate.

Other suitable photopolymerizable systems include those based on a multifunctional prepolymer mixture of 2,2-bis-(4-(2-hydroxy-3-methacryloyloxypropoxy)phenyl)propane, known commonly as "Bis-GMA." These compositions typically include a photoinitiation system, and can include other fillers, diluents, additives, and the like. These systems are described in, for example, U.S. Pat. Nos. 4,102,856, 4,131,729, 3,730,947, and 6,339,113, the disclosures of each of which are incorporated herein by reference in their entirety.

Scavengers such as magnesium oxide may be advantageously employed if it is desired to reduce or eliminate any adverse effects of by-products of the polymerization reaction. Inhibitors also may be included to control the exothermic generation of heat in some systems such that the temperature of the implant material upon curing, does not increase much above that of body temperature. Suitable inhibitors may include p-methoxyphenol and hydroquinone.

Hydrophilic polymers useful in forming the nucleus pulposus implant of embodiments of the invention include any now known or later discovered hydrophilic polymers. Non-limiting examples of hydrophilic polymers include, but are not limited to, polyacrylamide; polyacrylic acid; polyvinylpyrrolidone; copolymers of ethyleneoxide and propyleneoxide or hyaluronic acid; naturally-occurring materials such as collagen, gelatin, albumin, keratin, elastin, silk, hyaluronic acid and derivatives thereof, proteoglycan, glucomannan gel, and polysaccharides such as cross-linked carboxyl-containing polysaccharides; and combinations thereof.

Hydrophilic polymers may optionally also comprise, or alternatively consist of, one or more hydrogels or xerogels. Suitable hydrogels include natural hydrogels, and those formed from polyvinyl alcohol, acrylamides such as polyacrylic acid and poly(acrylonitrile-acrylic acid), polyurethanes, polyethylene glycol, poly(N-vinyl-2-pyrrolidone), polyacrylates such as poly(2-hydroxy ethyl methacrylate) and copolymers of acrylates with N-vinyl pyrrolidone, N-vinyl lactams, acrylamide, polyurethanes and polyacrylonitrile, and other similar materials that form a hydrogel, and combinations thereof. The hydrogel materials may further be cross-linked to provide further strength to the implant.

Additional components may be added to the polymer blend composition to further enhance the characteristics of the polymer composition. In one embodiment of the invention, elastomers are added to the polymer blend compositions. Non-limiting examples of elastomers that may be added to the polymer blend compositions include, but are not limited to, silicone, polyurethane, polybutadiene, polyolefins, such as polyisobutylene and polyisoprene, neoprene, nitrile, vulcanized rubber and combinations thereof. Vulcanized rubber may be produced, for example, by a vulcanization process utilizing a copolymer produced as described, for example, in U.S. Pat. No. 5,245,098, from 1-hexene and 5-methyl-1,4-hexadiene.

When an elastomeric polymer is used in combination with a thermoplastic silicone polyurethane polymer, the elastomer may be added to the polymer blend in concentrations comprising, or alternatively consisting of, about 5-40% (by weight) of the total weight of the polymer composition.

In another preferred embodiment of the invention, polyelectrolytes are added to the polymer blend composition to further enhance the hydrophilic nature of the nucleus pulposus implant. Non-limiting examples of polyelectrolytes that may be added to the spinal nucleus implant compositions include, but are not limited to, members of the following systems: proteins, nucleic acids, sulfonated styrene, and polyacrylic acids. Further examples include polymethacrylic acid, polystyrene sulfate, carboxymethylcellulose, xantham gum, pectins, polyallylamine hydrochloride, carrageenan, and combinations thereof. Polyelectrolytes are well known in the art, and one skilled in the art will appreciate still other examples of polyelectrolytes that may be used in the embodiments described herein.

Polyelectrolytes may be added to the polymer blend in concentrations comprising, or alternatively consisting of, about 5-100% (by weight) of the weight of the hydrophilic, when used in combination with another hydrophilic polymer. When used as the hydrophilic polymer component, the polyelectrolyte preferably is present in an amount ranging from about 5 to about 25 weight %, based on the total weight of the hydrophilic polymer.

In a preferred embodiment of the invention, the polymerizable material is introduced into the patient as an in situ curable composition. The curable material may be introduced into the patient using means known to those of skill in the art for introducing fluid materials such as, for example, catheters or syringes. In addition, a balloon or other type of mold device may be inserted into the at least partially evacuated disc space in a deflated condition. The curable material and hydrophilic polymer then may be inserted into the balloon or mold device to inflate the device and assume the configuration of the at least partially evacuated disc space. The balloon or mold device then can be sealed, or a self sealing fill valve may be used to effectively seal the inflatable material while the curable material cures in-situ.

Figure 1:
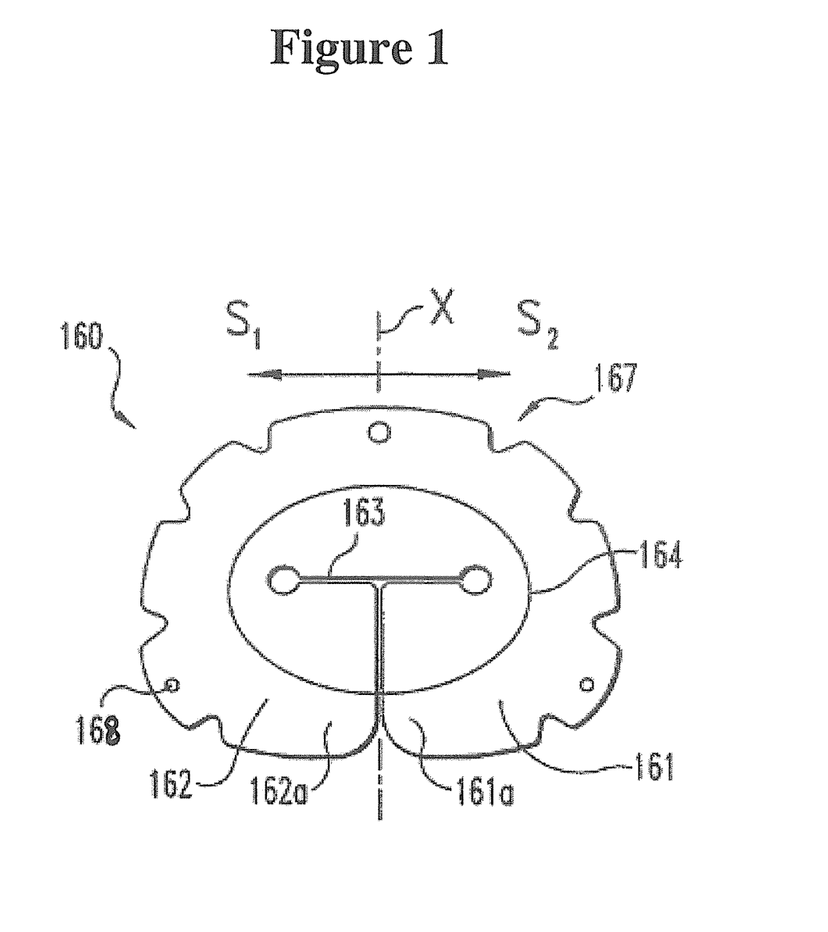
FIG. 1 shows one preferred embodiment of a disc nucleus implant that may be implanted according to one aspect of the present invention.
Figure 2:
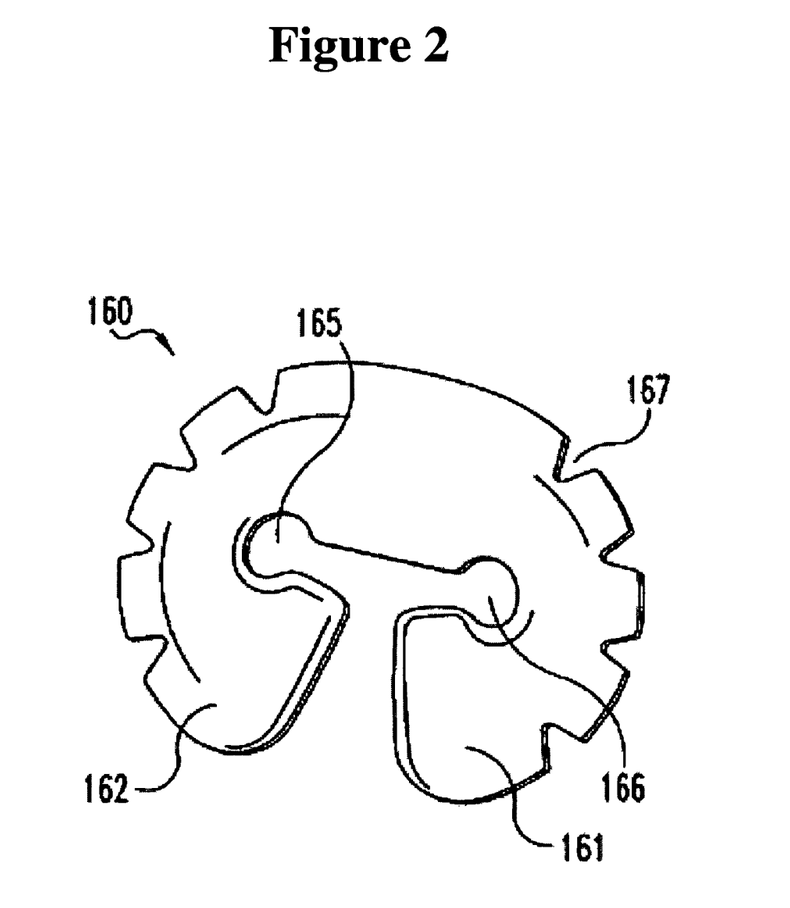
FIG. 2 shows the disc nucleus implant of FIG. 1 in a partially straightened configuration.
Figure 3:
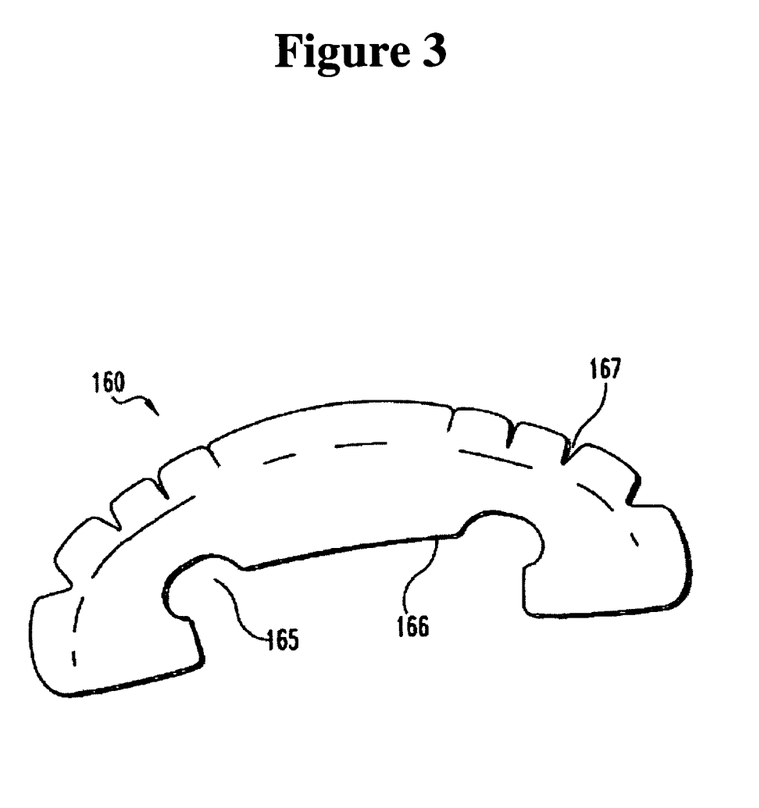
FIG. 3 shows the disc nucleus implant of FIG. 1 in a nearly straightened configuration.

In another embodiment of the invention, the curable material is formed into a solid implant ex vivo and implanted into the patient. In this embodiment, the implant is deformable such that the implant can be molded into an inherent shape, deformed into an insertion shape, or an indwelling shape following implantation, as shown in FIGS. 1-3, and described in more detail below. The molded shape may be spherical, cylindrical, helixical, ovate, or any other appropriate shape. The implant may have an angular, tapered shape similar to a three-dimensional trapezoid. Alternatively, the implant is molded into an elongated rod-like shape. In this embodiment, the respective ratios of the polymer blend composition can be varied, and the ultimate mixture of components (e.g., homogenous blend, heterogenous, etc.) may be modified to provide an implant having a variety of characteristics (e.g., more swelling on one side than the other, or more swelling in the middle, for example).

Following implantation, the rod adapts into a spiral shape. In another embodiment of the invention, the nucleus pulposus implant comprises a plurality of implants, each with a hole passing therethrough. The implants have angled ends so that, when the implants are positioned within the annulus fibrosus and pulled together, a "C"-shaped implant is formed.

Additionally, the polymer blend composition described herein may be a component of a multi-part or multi-layer implant. For example, the cured polymer blend composition may be the center of a nucleus implant surrounded by a fabric or another polymeric layer. The center of the multi-part implant may take any of the shapes discussed herein or any other appropriate shape for implantation, or assume any shape following injection of the polymer blend composition. In another embodiment of the invention, the cured polymer blend composition of the invention is the center layer of a three-layered nucleus implant. One possessing ordinary skill in the art, in light of known systems and methods, will appreciate the myriad implant configurations that may be produced.

When the nucleus pulposus implant is cured ex-vivo and implanted, a preferred delivery apparatus includes a cannula adapted to both contain and position the nucleus pulposus implant of the invention in a minimally invasive fashion. The dimensions of the cannula are selected according to the specific features of the tissue site. Accordingly, the longitudinal dimension, curvature, width or circumference of the cannula can vary. The delivery apparatus can further comprise a placement feature for use in positioning the implant. The placement tool can include an elongated rod having a plate or other device for positioning the implant, adapted to be movably contained within the cannula. The movement of the elongated rod is controlled by the surgeon and can be in the form of a syringe-like structure, a trigger, and the like. Accordingly, when pushed forward, the placement tool expels or ejects the nucleus pulposus implant from the distal end of the cannula into the evacuated annulus fibrosus. A suitable delivery device is disclosed in U.S. Patent Application Publication No. 2004/0117019 (application Ser. No. 10/717,687), the disclosure of which is incorporated by reference herein in its entirety.

FIGS. 1-3 illustrate one preferred embodiment of a disc nucleus implant that may be implanted with a disc delivery instrument. Nucleus pulposus implant 160 preferably is molded into a "C" configuration, and comprises a pair of arms 161 and 162 that are folded to form an inner fold 163 when the implant is in its relaxed configuration. The folded arms abut one another at their ends 161a and 162a when the implant is relaxed, so that the center core 164 of the implant (when viewed from above as in FIG. 1) is substantially solid.

Apertures 165 and 166 can be included to correspond to posts present on a disc delivery instrument (not shown) similar to that described in U.S. Patent Application Publication No. 2004/0117019. When the posts are inserted into the apertures and the hinged channel members are pivoted to an angle of about 180°, implant 160 straightens to provide a cross sectional size that is less than the cross sectional size of the folded implant. Grooves 167 are provided on the outer surface to prevent cracking or tearing of the implant when the implant is in its straightened configuration. X-ray markers such as tantalum markers 168 may be included to assist in positioning the implant. Preferably, a larger x-ray marker is provided in the anterior portion of the implant, and smaller x-ray markers are provided in posterior portions of the implant.

The nucleus pulposus implant may further comprise therapeutics, such as a pharmacological agent or biological agent. Examples of pharmacological agents or biological agents include, but are not limited to, antibiotics, analgesics, anti-inflammatory drugs, steroids, anti-viral and anti-retroviral compounds, therapeutic proteins or peptides, and therapeutic nucleic acids (as naked plasmid or a component of an integrating or non-integrating gene therapy vector system).

Antibiotics useful with the nucleus pulposus implants include, but are not limited to, amoxicillin, beta-lactamases, aminoglycosides, beta-lactam (glycopeptide), clindamycin, chloramphenicol, cephalosporins, ciprofloxacin, erythromycin, fluoroquinolones, macrolides, metronidazole, penicillins, quinolones, rapamycin, rifampin, streptomycin, sulfonamide, tetracyclines, trimethoprim, trimethoprim-sulfamthoxazole, and vancomycin. In addition, one skilled in the art of implant surgery or administrators of locations in which implant surgery occurs may prefer the introduction of one or more of the above-recited antibiotics to account for nosocomial infections or other factors specific to the location where the surgery is conducted. Accordingly, the invention further contemplates that one or more of the antibiotics recited supra, and any combination of one or more of the same antibiotics, may be included in the nucleus pulposus implants of the invention.

The invention further contemplates the inclusion of immunosuppressives as a component contained within the nucleus pulposus implants. Suitable immunosuppressive agents that may be administered in combination with the nucleus pulposus implant include, but are not limited to, steroids, cyclosporine, cyclosporine analogs, cyclophosphamide, methylprednisone, prednisone, azathioprine, FK-506, 15-deoxyspergualin, and other immunosuppressive agents that act by suppressing the function of responding T cells. Other immunosuppressive agents that may be administered in combination with the nucleus pulposus implants include, but are not limited to, prednisolone, methotrexate, thalidomide, methoxsalen, rapamycin, leflunomide, mizoribine (bredinin™), brequinar, deoxyspergualin, and azaspirane (SKF 105685), Orthoclone OKT™ 3 (muromonab-CD3). Sandimmune™, Neoral™, Sangdya™ (cyclosporine), Prograf™ (FK506, tacrolimus), Cellcep™ (mycophenolate motefil, of which the active metabolite is mycophenolic acid), Imuran™ (azathioprine), glucocorticosteroids, adrenocortical steroids such as Deltasone™ (prednisone) and Hydeltrasol™ (prednisolone), Folex™ and Mexate™ (methotrxate), Oxsoralen-Ultra™ (methoxsalen) and Rapamuen™ (sirolimus).

The invention also contemplates the use of therapeutic polynucleotides or polypeptides (hereinafter "therapeutics") with the nucleus pulposus implants of the invention. As noted supra, the therapeutics are administered as proteins or peptides, or therapeutic nucleic acids, and may be administered as full length proteins, mature forms thereof or domains thereof, as well as the polynucleotides encoding the same. Examples of therapeutic polypeptides include, but are not limited to, Bone Morphogenetic Proteins (BMPs), including BMP-1, BMP-2, BMP-3, BMP-4, BMP-5, BMP-6, BMP-7, BMP-8, BMP-9, BMP-10, BMP-1, BMP-12, BMP-13, BMP-15, BMP-16, BMP-17, and BMP-18; Vascular Endothelial Growth Factors (VEGFs), including VEGF-A, VEGF-B, VEGF-C, VEGF-D and VEGF-E; Connective Tissue Growth Factors (CTGFs), including CTGF-1, CTGF-2, and CTGF-3; Osteoprotegerin, Transforming Growth Factor betas (TGF-βs), including TGF-β-1, TGF-β-2, and TGF-β-3; inhibitors for tumor necrosis factor (e.g., anti-TNFα); and Platelet Derived Growth Factors (PDGFs), including PDGF-A, PDGF-B, PDGF-C, and PDGF-D. The polynucleotides encoding the same may also be administered as gene therapy agents.

In a particularly preferred embodiment of the invention, the nucleus pulposus implant comprises antagonists to either Nogo-A, the largest transcript of the recently identified nogo gene (formerly called NI-220) which is present in CNS myelin and has been characterized as a potent inhibitor of axonal growth, or antagonists to the Nogo receptor subunit NgR. For example, Nogo-A acts as a potent neurite growth inhibitor in vitro and represses axonal regeneration and structural plasticity in the adult mammalian CNS in vivo. In another embodiment of the invention, antagonists to both Nogo-A and the Nogo receptor subunit NgR are co-administered to the patient. In this preferred embodiment of the invention, the nucleus pulposus implants of the invention are used as implants for intervertebral discs that are adjacent locations of spinal cord injury, and may also replace damaged or infected endogenous nucleus pulposus. In this embodiment of the invention, the inhibitory activity of the antagonist(s) to the activity of the Nogo receptor subunit NgR and Nogo-A may aid in the regeneration of damaged spinal nerve tissue, and the nucleus pulposus implant serves as a local reservoir of therapeutic antagonist(s) to aid in the growth of damaged spinal tissue. Antagonists of the Nogo receptor subunit NgR and Nogo-A may take the form of monoclonal antibodies, binding peptides, anti-sense molecules, small molecule antagonists, and any other forms of protein antagonists known to those of skill in the art.

In this embodiment, therapeutic polypeptides or polynucleotides of Ninjurin-1 and Ninjurin-2 may further be administered alone or in conjunction with one or more NgR or Nogo-A antagonists, as a component of the nucleus pulposus implant. Ninjurin-1 and Ninjurin-2 are believed to promote neurite outgrowth from primary cultured dorsal root ganglion neurons. Ninjurin-1 is a gene that is up-regulated after nerve injury both in dorsal root ganglion (DRG) neurons and in Schwann cells. The full-length proteins, mature forms or domains of the full-length proteins thereof may be administered as therapeutics, as well as the polynucleotides encoding the same.

The invention further contemplates a method of treating spinal cord injury using the nucleus pulposus implants of the invention as a reservoir for therapeutic agents that promote the growth of injured spinal cord tissue or damaged nerves, comprising administering at least one or more, including all, of the above-recited therapeutics as a component of the nucleus pulposus implants of the invention. In one embodiment of the invention, the nucleus pulposus implant material includes the therapeutic agents admixed with the implant compositions. The therapeutic agents may be administered to the nucleus pulposus implant in any number of suitable fluids, such as for example, water and saline solution.

The polymer blend compositions preferably include blends of a prepolymer admixed with a curative agent, and a hydrophilic compound, and can be produced using techniques known in the art. Methods of synthesizing the prepolymer and curative agent components of the polymer blend compositions are known to those of skill in the art, and are based on the prepolymer and curative agent composition ultimately selected for synthesis. Hydrophilic compounds may be added to the fluid polymer blend composition, and preferably are mixed to a nearly confluent blend, prior to introduction to the patient. Methods of synthesizing or obtaining the hydrophilic compound are known to those of skill in the art, and are based on the hydrophilic compound ultimately selected for use in the polymer blend composition.

In the event the polymer blend composition is cured in a mold prior to implantation, molds may be made of a metal such as aluminum, steel, iron, and mixtures thereof, or alternatively could be made of a ceramic. The size of the implant mold can be determined for each individual patient prior to production of the implant.

Methods of obtaining or producing the curable polymerizable material, as well as the hydrophilic polymers, is within the scope of a skilled artisan, and techniques for the production of these compounds is available in the patent and scientific literature. Accordingly, using the guidelines provided herein, skilled artisans are capable of forming a suitable nucleus pulposus implant composition including at least a curable polymer material and at least one hydrophilic material.

Methods of producing therapeutic polynucleotides and polypeptides that are co-administered with the nucleus pulposus implants are well known to one of skill in the art. The present invention contemplates vectors containing the therapeutic polynucleotides recited supra, host cells, and the production of therapeutic polypeptides by recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells. Useful vectors include, but are not limited to, plasmids, bacteriophage, insect and animal cell vectors, retroviruses, cosmids, and other single and double-stranded viruses.

The polynucleotide insert should be operatively linked to an appropriate promoter, such as the phage lambda PL promoter, the E. coli lac, trp, phoA and tac promoters, the SV40 early and late promoters and promoters of retroviral LTRs, to name a few. Other suitable promoters will be known to the skilled artisan. The expression constructs will further contain sites for transcription initiation, termination; origin of replication sequence, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

The expression construct may further contain sequences such as enhancer sequences, efficient RNA processing signals such as splicing and polyadenylation signals, sequences that enhance translation efficiency, and sequences that enhance protein secretion.

Expression systems and methods of producing therapeutics, such as recombinant proteins or protein fragments, are well known in the art. For example, methods of producing recombinant proteins or fragments thereof using bacterial, insect or mammalian expression systems are well known in the art. (See, e.g., Molecular Biotechnology: Principles and Applications of Recombinant DNA, B. R. Glick and J. Pasternak, and M. M. Bendig, Genetic Engineering, 7, pp. 91-127 (1988), for a discussion of recombinant protein production).

The expression vectors preferably will include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate host cells for expression include, but are not limited to, bacterial cells, such as *E. coli, Streptomyces* and *Salmonella typhimurium* cells; fungal cells, such as *Pichia, Saccharomyces* and other yeast cells; insect cells such as *Drosophila* S2 and *Spodoptera* Sf9 and Sf21 cells; animal cells such as CHO, COS, 293, and Bowes melanoma cells; and plant cells. Appropriate culture mediums and conditions for the above-described host cells are known in the art.

Examples of vectors for use in prokaryotes include pQE30Xa and other pQE vectors available as components in pQE expression systems available from QIAGEN, Inc. (Valencia, Calif.); pBluescript vectors, Phagescript vectors, pNH8A, pNH16a, pNH18A, pNH46A, available from Stratagene Cloning Systems, Inc. (La Jolla, Calif.); and Champion™, T7, and pBAD vectors available from Invitrogen (Carlsbad, Calif.). Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986).

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

In another embodiment of the invention, therapeutic agents can be produced using bacterial lysates in cell-free expression systems that are well known in the art. Commercially available examples of cell-free protein synthesis systems include the EasyXpress System from Qiagen, Inc. (Valencia, Calif.).

Therapeutics can also be recovered from the following: products of chemical synthetic procedures; and products produced by recombinant techniques from a prokaryotic or eukaryotic host, including, for example, bacterial, yeast, higher plant, insect, and mammalian cells.

Depending upon the host employed in a recombinant production procedure, therapeutics may be glycosylated or may be non-glycosylated. In addition, therapeutics may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

Therapeutics also may be isolated from natural sources of polypeptide. Therapeutics may be purified from tissue sources, preferably mammalian tissue sources, using conventional physical, immunological and chemical separation techniques known to those of skill in the art. Appropriate tissue sources for the desired therapeutics, or other techniques for obtaining the recited therapeutics such as PCR techniques, are known or are available to those of skill in the art.

The invention also encompasses methods of treating spinal injury in which the nucleus pulposus contributes to the development of the disease, such as for example a herniated disc, by replacing the endogenous nucleus pulposus material.

In one embodiment of the invention, the dysfunctional intervertebral disc is accessed surgically and at least a portion of the endogenuos nucleus pulposus material and any free disc fragments are removed. Subsequently, the polymer blend composition of the invention is delivered to the evacuated annulus fibrosus. Delivery of the polymer blend composition to the annulus fibrosus may be achieved, for example, using minimally invasive surgical techniques and devices. Therefore, the polymer blend composition may be delivered via a cannula or syringe to the evacuated nucleus. An optional inflatable member also may be delivered to the at least partially evacuated nucleus, which in turn may be inflated upon injection of the polymer blend composition of the invention. The appropriate delivery method is selected by a surgeon skilled in the art of intervertebral disc repair and replacement.

In another embodiment of the invention, the polymer blend compositions of the invention are useful in the prevention or treatment, or for aiding in the prevention or treatment, of diseases and/or disorders associated with the spinal column. Non-limiting examples of diseases and/or disorders that the polymer blend compositions of the invention are useful in preventing or treating include, but are not limited to: bulging disc(s); herniated disc(s); spinal injury due to trauma; age-related degeneration or failure of spinal column components (namely intervertebral disc(s)); spinal instability; discogenic back pain; intervertebral osteochondrosis; spondylolisthesis; spinal infection; spinal tumors; and arthritis of the spine.

In one embodiment of the invention, the polymer blend compositions are administered to the patient in substantially admixed form and cure in situ, and absorb water and swell after administration to the patient and curing in situ. Following hydration of the cured polymer blend composition of the invention, the hydrated nucleus pulposus compositions substantially fill the at least partially evacuated cavity of the disc.

The exact size of the replacement nucleus pulposus, when fully hydrated, can be varied for different individuals. A typical size of an adult nucleus pulposus is 2 cm in the semi-minor axis, 4 cm in the semi-major axis and 1.2 cm in thickness. The invention contemplates numerous sizes for the nucleus pulposus implant to accommodate different sizes of individual patients, relative to the typical size set forth above.

The curable polymer blend compositions of the invention occupy at least 50% of the evacuated intervertebral disc space, preferably 70% of the intervertebral disc space, even more preferably 80% of the intervertebral disc space, even more preferably 90% of the intervertebral disc space, and even more preferably 99% or more of the intervertebral disc space. The appropriate size of the implant volume can be determined for a particular patient by measuring the volume of an evacuated annulus fibrosus with an injectable saline balloon.

In an additional aspect of the invention, the polymer blend composition of the invention is packaged in kits under sterile conditions prior to implantation into a patient. In one embodiment of the invention, the polymer blend composition of the invention is included as a component of a surgical kit for implantation, along with minimally invasive surgical tools or instruments such as a catheter. Generally, the kit comprises the polymer blend composition of the invention together with a minimally invasive delivery apparatus. The kit may include two containers containing two components of the polymer mixture that cure shortly after mixing, and an additional container containing the hydrophilic portion of the polymer blend, together with additives. Alternatively, the hydrophilic portion and other additives may be added to the curable polymer portion. The kit also may include an inflatable member that can be inserted into the at least partially evacuated disc space using minimally invasive means, as well as various surgical tools to effect the necessary operation and delivery of the respective components to the surgical site.

A preferred delivery apparatus includes a cannula adapted to both contain and position the polymer blend composition of the invention in a minimally invasive fashion. The dimensions of the cannula are selected according to the specific features of the tissue site. Accordingly, the longitudinal dimension, curvature, width or circumference of the cannula can vary. A more preferred delivery apparatus includes a syringe and a suitable gauge needle for injecting the curable polymer material and hydrophilic polymer material to the appropriate position in the patient.

The invention may be practiced in ways other than those particularly described in the foregoing description and examples. Numerous modifications and variations of the invention are possible in light of the above teachings and, therefore, are within the scope of the appended claims.

The entire disclosure of each document cited (including patents, patent applications, journal articles, abstracts, manuals, books, or other disclosures) in the Background of the Invention, Detailed Description, and Examples is herein incorporated by reference in their entireties.

EXAMPLES

I. Production of a Nucleus Pulposus Implant

A prepolymer comprised of 2,4'-diphenylmethane diisocyanate is placed in one container at a concentration of 42.5%. The curative agent polytetrahydrofuran polyol is placed in a second container at a concentration of 42.5%. The hydrophilic polymer (polyvinyl alcohol) is added to the prepolymer 2,4'-diphenylmethane diisocyanate at a concentration of 5%, which is about 1/19 the concentration of the prepolymer and the curative agent combined. Additionally, an elastomer silicone and a polyelectrolyte polyacrylic acid are added to the prepolymer 2,4'-diphenylmethane diisocyanate, each at concentrations of 5% by weight of the total weight of the polymer blend composition.

When production of the nucleus pulposus is desired, the prepolymer (including the hydrophilic component, the elastomer component and the polyelectrolyte component) is combined with the curative agent, thoroughly admixed, and administered to the desired location to allow for in situ curing of the polymer blend composition.

II. Implantation of a Nucleus Pulposus Implant

A patient suffering from a herniated disc undergoes corrective surgery, which includes removal of at least some of the endogenous nucleus pulposus material, along with any free disc fragments, from the disc space, thereby leaving an at least partially evacuated intervertebral disc space. The appropriate size of the implant is determined for the patient by measuring the volume of the evacuated disc space with an inflatable saline balloon. A polymer blend composition similar to the composition of Example I is produced that cures in situ and, when cured and fully hydrated, occupies up to at least about 99% of the evacuated disc space.

The polymer blend composition is introduced into the evacuated disc space using delivery devices well known in the art, for example, syringes that contain the polymer blend composition. The polymer blend composition comprises at least one appropriate antibiotic prior to implantation in the patient. Following implantation, the annulus fibrosus may be surgically closed, if required, and the polymer blend composition is allowed to cure in situ.

The patient recovers after surgery, allowing the nucleus pulposus implant to achieve complete hydration. If necessary, the stability of the nucleus pulposus implant is evaluated using Magnetic Resonance Imaging (MRI) analysis.

What is claimed is:

1. An in-situ three-part formable nucleus pulposus implant composition, comprising a first part, a second part and a third part that when mixed together in-situ provides a cured polyurethane implant;
   said first part comprising an in-situ curable polymerizable material comprising 2,4'-diphenylmethane diisocyanate, 4,4'-diphenylmethane diisocyanate, and toluene diisocyanate;
   said second part comprising at least one hydrophilic polymer, wherein the polymerizable material and the at least one hydrophilic polymer are present in a ratio of about 1:1 to about 19:1, respectively, the hydrophilic polymer comprising at least one of polyacrylic acid, polyacrylamides, or poly(N-vinyl-2-pyrrolidone),
   said third part comprising at least one therapeutic agent selected the group consisting of antibiotics, analgesics, anti-inflammatory drugs, steroids, anti-viral and anti-retroviral compounds, therapeutic proteins, therapeutic peptides, and therapeutic nucleic acids; and
   wherein said in-situ three-part formable composition polymerizes inside a partially evacuated intervertebral disc space to form a polymerized implant.

2. The composition according to claim 1, wherein the polymerizable material and the at least one hydrophilic polymer are present in a ratio of about 9:1, respectively.

3. The composition of claim 1, wherein the at least one hydrophilic polymer is selected from the group consisting of collagen, gelatin, albumin, keratin, elastin, silk, hyaluronic acid and derivatives thereof, proteoglycan, glucomannan gel, polysaccharides, and combinations thereof.

4. The composition of claim 1, wherein the at least one hydrophilic polymer is a hydrogel selected from the group consisting of polyvinyl alcohol, poly(acrylonitrile-acrylic acid), polyurethanes, polyethylene glycol, polyethyleneoxide, polyacrylates, poly(2-hydroxy ethyl methacrylate), copolymers of acrylates with N-vinyl pyrrolidone, N-vinyl lactams, acrylamide, polyurethanes, and combinations thereof.

5. The composition of claim 1, further comprising an elastomer material.

6. The composition of claim 5, wherein the elastomer is selected from the group consisting of silicone, polyurethane, polybutadiene, polyolefins, such as polyisobutylene and polyisoprene, neoprene, nitrile, vulcanized rubber and combinations thereof.

7. The composition of claim 5, wherein the elastomer is present in a concentration of about 5-40% by weight of the total composition.

8. The composition of claim 1, further comprising a polyelectrolyte.

9. The composition of claim 8, wherein the polyelectrolyte is selected from the group consisting of proteins, nucleic acids, sulfonated styrene, polyacrylic acids, and combinations thereof.

10. The composition of claim 8, wherein the polyelectrolyte is selected from the group consisting of carboxymethylcellulose, polyacrylic acid, xantham gum, pectins, polystyrene sulfate, polymethacrylic acid, polyallylamine hydrochloride, carrageenan, and combinations thereof.

11. The composition of claim 8, wherein the polyelectrolyte is present in a concentration of about 5-100% by weight of the hydrophilic polymer.

12. The composition of claim 1, wherein said antibiotics is selected from the group consisting of amoxicillin, beta-lactamases, aminoglycosides, beta-lactam (glycopeptide), clindamycin, chloramphenicol, cephalosporins, ciprofloxacin, erythromycin, fluoroquinolones, macrolides, metronidazole, penicillins, quinolones, rapamycin, rifampin, streptomycin, sulfonamide, tetracyclines, trimethoprim, trimethoprim-sulfamthoxazole, and vancomycin.

13. The compositions of claim 1 wherein said therapeutic nucleic acids encode proteins/peptides selected from the group consisting of Bone Morphogenetic Proteins (BMPs), including BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, and MBP-18; Vascular Endothelial Growth Factors (VEGFs), including VEGF-A, VEGF-B, VEGF-C, VEGF-D and VEGF-E; Connective Tissue Growth Factors (CTGFs), including CTGF-1, CTGF-2, and CTGF-3; Osteoprotegerin, Transforming Growth Factor betas (TGF-βs), including TGF-β1, TGF-β2, TGF-β3; inhibitors for tumor necrosis factor (e.g., anti-TNFα); and Platelet Derived Growth Factors (PDGFs), including PDGF-A, PDGF-B, PDGF-C, and PDGF-D.

14. A method of treating or preventing a spinal disease or disorder, comprising
   a) surgically evacuating at least a portion of nucleus pulposus material and any free disc fragments from at least one intervertebral disc of a patient;
   b) providing the three-part formable nucleus pulposus implant composition of claim 1; and
   c) implanting each of the parts of said three-part formable nucleus pulposus implant composition of claim 1 separately into the at least partially evacuated intervertebral disc space of the patient whereby the in-situ three-part formable polymer composition polymerizes inside the partially evacuated intervertebral disc space to form a polymerized implant.

15. The method of claim 14, further comprising measuring the volume of the at least partially evacuated intervertebral disc space by an inflatable saline balloon prior to preparing implanting the polymer blend composition.

16. The method of claim 14, wherein the spinal disease or disorder is selected from the group consisting of bulging disc(s); herniated disc(s); spinal injury due to trauma; age-related degeneration or failure of spinal column components; spinal instability; discogenic back pain; intervertebral osteochondrosis; spondylolisthesis; spinal infection; spinal tumors; arthritis of the spine, and any combination or combinations thereof.

17. The method of claim 14, wherein the polymerizable material is a polyfunctional isocyanate based polymerizable material.

18. The method of claim 14, wherein the polymerizable material is a-three-part polymerizable material.

19. The method of claim 18, wherein the two-part polymerizable material forms a polyurethane and has as one part a diisocyanate or polymeric isocyanate and as the other part a polyol.

20. The method of claim 19, wherein said diisocyanate is 2,4-toluene diisocyanate or 2,6-toluene diisocyanate, and said in-situ curable polymerizable a mixture further comprises 2,2' diphenylmethane diisocyanate.

21. The method of claim 19, wherein the polyol is selected from the group consisting of polycaprolactone polyols, polycarbonate polyols, polyester polyols, polytetrahydrofuran polyol, and mixtures thereof.

22. The method of claim 18, wherein a catalyst is added to one of the three parts of the polymerizable material forming a polyurethane.

23. The method of claim 22, wherein the catalyst is selected from the group consisting of tin esters, tin alkylesters, tin mercaptides, amines, tertiary amines, dibutyl tin dilaurate, and mixtures thereof.

24. The method of claim 18, wherein low molecular weight diols are added to one part of the three-part polymerizabie material forming a polyurethane.

25. The method of claim 14, wherein the polymerizabie material is a light activated polymerizabie material.

26. The method of claim 25, wherein the light activated polymerizabie material comprises a mixture of a polyfunctional urethane acrylate or polyfunctional urethane methacrylate and a polyfunctional acrylate resin.

27. The method of claim 25, wherein the light activated polymerizabie material comprises a mixture of 2,2-bis-(4-(2-hydroxy-3-methacryloyloxypropoxy)phenyl) propane and a photoinitiation system.

28. The method of claim 25, wherein the light activated polymerizabie material comprises a one part system of triisocyanates or higher isocyanates and OH-functional acrylates or methacrylates.

29. The method of claim 14, wherein the polymerizabie material is a heat activated polymerizabie material.

30. The method of claim 14, wherein the polymerizabie material is a water activated polymerizabie material.

31. The method of claim 30, wherein the water activated polymerizabie material is a siloxane with a functional group that allows polymerization of the siloxane with water.

32. The method of claim 31, wherein the water activated siloxane has alkoxy, acyloxy, acetoxy, amido, oximo, or amino functional groups.

33. The method of claim 30, wherein the water activated polymerizabie material is a polyfunctional isocyanate based polymerizabie material.

34. The method of claim 14, wherein the polymerizabie material is self-curable.

* * * * *